(12) United States Patent
Dingeldein et al.

(10) Patent No.: US 9,561,305 B2
(45) Date of Patent: Feb. 7, 2017

(54) HYDROXYLAPATITE MATERIAL, AND METHOD FOR THE PRODUCTION THEREOF

(75) Inventors: Elvira Dingeldein, Moenchberg (DE); Lydia Heimann, Hoesbach (DE); Georgiana Gasqueres, Aschaffenburg (DE); Marco Wolfstadter, Worth/Main (DE)

(73) Assignee: AAP BIOMATERIALS GMBH, Dieburg (DE)

( * ) Notice: Subject to any disclaimer, the term of this patent is extended or adjusted under 35 U.S.C. 154(b) by 132 days.

(21) Appl. No.: 13/393,927

(22) PCT Filed: Sep. 2, 2010

(86) PCT No.: PCT/EP2010/005383
§ 371 (c)(1),
(2), (4) Date: Jun. 25, 2012

(87) PCT Pub. No.: WO2011/026618
PCT Pub. Date: Mar. 10, 2011

(65) Prior Publication Data
US 2012/0265152 A1   Oct. 18, 2012

(30) Foreign Application Priority Data

Sep. 2, 2009 (DE) .......... 10 2009 039 665

(51) Int. Cl.
*C01B 25/32* (2006.01)
*A61L 27/12* (2006.01)

(52) U.S. Cl.
CPC .............. *A61L 27/12* (2013.01); *C01B 25/327* (2013.01); *A61L 2400/12* (2013.01); *Y10T 428/2982* (2015.01)

(58) Field of Classification Search
CPC ..... A61L 27/12; A61L 2400/12; A61K 35/32; A61K 9/14; C01B 25/32
See application file for complete search history.

(56) References Cited

U.S. PATENT DOCUMENTS

| 2,658,832 A | * | 11/1953 | De Ment .......................... 106/35 |
| 6,013,591 A | * | 1/2000 | Ying et al. ......................... 501/1 |
| 6,506,217 B1 | | 1/2003 | Arnett |
| 6,689,375 B1 | * | 2/2004 | Wahlig et al. ................. 424/426 |
| 7,670,384 B2 | * | 3/2010 | Kumar et al. .............. 623/23.63 |

FOREIGN PATENT DOCUMENTS

| DE | 35 13 144 | 3/1986 |
| EP | 0664133 | 7/1995 |
| WO | WO 99/20237 | 8/2000 |
| WO | WO 02/22117 | 3/2002 |

OTHER PUBLICATIONS

Z. Zyman et al. Nonstoichiometric hydroxyapatite granules for orthopaedic applications, Journal of materials scinecne: materials in medicine 15, 551-558, 2004.*
Nasser Y. Mostafa, Characterization, thermal stability and sintering of hydroxyapatite powders prepared by different routes, Material Chemistry and Physics, 94, 333-341, 2005.*
European Pharmacopoeia 6, pp. 445-447, 2011.
International Preliminary Report of Patentability (Chapter I) issued for PCT/EP2010/005383, dated Mar. 27, 2012.
International Search Report issued for PCT/EP2010/005383, dated Apr. 15, 2011.

* cited by examiner

*Primary Examiner* — Michael G Hartley
*Assistant Examiner* — Jagadishwar Samala
(74) *Attorney, Agent, or Firm* — Pearl Cohen Zedek Latzer Baratz LLP (57) ABSTRACT

The invention relates to a hydroxylapatite material, for the production of which a nanoscale hydroxylapatite paste is subjected to a thermal treatment.

6 Claims, 9 Drawing Sheets

| Temperature (°C) | Sintering duration (h) | Particle size (mm) | Crystallite size L (002) (2θ = 25.9°) in nm | Crystallite size L (213) (2θ = 40.5°) in nm |
|---|---|---|---|---|
| 600 | 2 | 0.5-1.0 | 24 | 20 |
| 600 | 2 | 1.0-2.0 | 25 | 23 |
| 700 | 2 | 0.5-1.0 | 26 | 27 |
| 700 | 2 | 1.0-2.0 | 28 | 26 |
| 850 | 2 | 0.5-1.0 | 33 | 34 |
| 850 | 2 | 1.0-2.0 | 36 | 34 |
| 950 | 4 | 0.5-1.0 | 40 | 40 |
| 950 | 4 | 1.0-2.0 | 44 | 40 |

HYDROXYLAPATITE MATERIAL, AND METHOD FOR THE PRODUCTION THEREOF

CROSS-REFERENCE TO RELATED APPLICATIONS

This application is a National Phase Application of PCT International Application PCT/EP2010/005383, filed Sep. 2, 2010, that claims priority to German Patent Application DE 10 2009 039 665.9, filed Sep. 2, 2009, both of which are incorporated by reference herein in their entirety.

FIELD OF THE INVENTION

The invention relates to a hydroxylapatite material and to a method for producing same.

BACKGROUND OF THE INVENTION

Hydroxyapatite is known as a bone substitute material.

In particular, nanoscale hydroxylapatite, i.e. hydroxylapatite having a mean particle size of less than 100 nm, is known and is being used as a paste for treating bone defects. In particular, hydroxylapatite is used which has a length of less than 200 nm as measured in a longitudinal direction of the particles. The particles are needle- or rod-shaped and have a small thickness of preferably less than 50 nm.

Also known are compressed or sintered form bodies made of hydroxylapatite which may be used as an implant.

Known hydroxylapatite pastes have the drawback of exhibiting a relatively low form stability which means that in many instances the paste is only suitable to a limited extent since it might be re-pressed out of the defect site after having been introduced, due to mechanical stresses. Moreover, handling of such pastes is often difficult.

Sintered bodies of hydroxylapatite, on the other hand, lack flexibility and are generally replaced only slowly by natural bone material.

Object of the Invention

Therefore, an object of the invention is to provide a hydroxylapatite material which is easy to handle and which is especially suitable for treating defects in the region of the jaw ridge.

Another object of the invention is to improve dissolubility compared to known sintered hydroxylapatite bodies.

The hydroxylapatite material shall exhibit good degradation and also good wetting and cohesive characteristics.

BRIEF DESCRIPTION OF THE DRAWINGS

FIG. 1 a shows a microscopic view of starting material (nanoscale hydroxylapatite).

FIG. 1 b shows a microscopic view of one embodiment of a hydroxylapatite granulated material according to the invention.

SUMMARY OF THE INVENTION

The object of the invention is already solved by a method for producing a hydroxylapatite material and by a form-stable hydroxylapatite material according to any of the independent claims.

Preferred embodiments and refinements of the invention are set forth in the respective dependent claims.

According to one aspect, the invention relates to a method for producing a hydroxylapatite material, in particular a granulated material.

Nanoscale hydroxylapatite is used as a starting material, and in form of a paste. Nanoscale hydroxylapatite is to be understood as hydroxylapatite having a particle size of less than 100 nm, or of less than 200 nm in the longitudinal extension when using rod- or needle-shaped particles.

Needle-shaped hydroxylapatite particles are preferred. Such particles and their preparation are described, for example, in European patent EP 1023035 B1, in European patent EP 1317261 B1, and in European patent EP 0664133 B1. The disclosures of these documents is entirely incorporated herein by reference. It is especially suggested to use, as a starting material, a nanoscale hydroxylapatite as described in any of these documents or prepared according to the teachings thereof.

It will be understood that in the context of the invention 'nanoscale hydroxylapatite' is intended to designate the particle size of individual particles as they appear in transmission electron microscopy. It is not meant to refer to any agglomerates that might be formed especially in highly concentrated hydroxylapatite suspensions due to agglomeration of individual particles.

According to the invention, the nanoscale hydroxylapatite is annealed at a temperature between 400 and 1300° C., preferably between 500 and 1100° C., and more preferably between 600 and 1000° C., i.e. it is subjected to a thermal treatment. In particular, the annealing temperature is from 600 to 950° C.

It has been found that by annealing the hydroxylapatite at a temperature which is below the normal sintering temperature for providing hydroxylapatite form bodies, a slight crystal growth results so that a form-stable hydroxylapatite material is produced.

The hydroxylapatite material is particularly provided as a form-stable granulated material which can be introduced into the defect site by means of an appropriate application tool. When compared to brittle sintered material, the granulated material produced according to the method of the invention is softer and exhibits significantly better cohesive properties. So, using an appropriate tool, defect sites can be filled up in a particularly simple manner.

The desired properties, depending on the application purpose, can be set via the annealing temperature and duration of the annealing process. Generally, a high temperature and a long holding time result in a larger crystal size. The inventors can demonstrate that the typically needle-shaped crystals of the nanoscale hydroxylapatite combine into larger crystals. In particular, interconnecting dumbbell-shaped and/or scale-like structures are formed.

Preferably a hydroxylapatite paste, i.e. a highly concentrated hydroxylapatite suspension, is used for annealing.

In particular a paste having a solids content from 10 to 60%, preferably from 30 to 50% is used.

In one embodiment of the invention, the paste is formed into granules prior to annealing. That means, granule preform bodies are produced from the paste, which are solidified in a subsequent annealing step.

The water content of the paste can be adjusted such that on the one hand the paste is easily processed by a granulator, and on the other hand is sufficiently viscous so that the produced granulate grains will not run.

In an alternative embodiment of the method, blocks, especially sheets, of a hydroxylapatite paste are annealed and then are broken, in particular ground, to a granulated material.

Furthermore, the invention relates to a method for producing a hydroxylapatite material, wherein the hydroxylapatite paste is formed into a preform body which defines the shape of an implant. So in this embodiment of the invention a form body of a paste is provided using a suitable mold, which form body is annealed. It goes without saying that annealing may involve a reduction of the volume.

In a preferred embodiment of the invention, the holding time is between 30 minutes and 10 hours, preferably between 2 and 4 hours.

The inventors have found that the thermal treatment may be performed at atmospheric pressure, in particular under air atmosphere. It is therefore not necessary, though possible, to apply a vacuum or to use an inert gas.

Preferably, a nanoscale hydroxylapatite having an average particle size of less than 200 nm, in particular of about 100 nm as measured in a longitudinal extension, is used. Preferably, the hydroxylapatite crystals have a substantially needle-shaped form which means they are longer in one spatial direction than in the two other spatial directions.

The invention also relates to a hydroxylapatite material which is producible and in particular is produced by the method described above.

Figure 12:
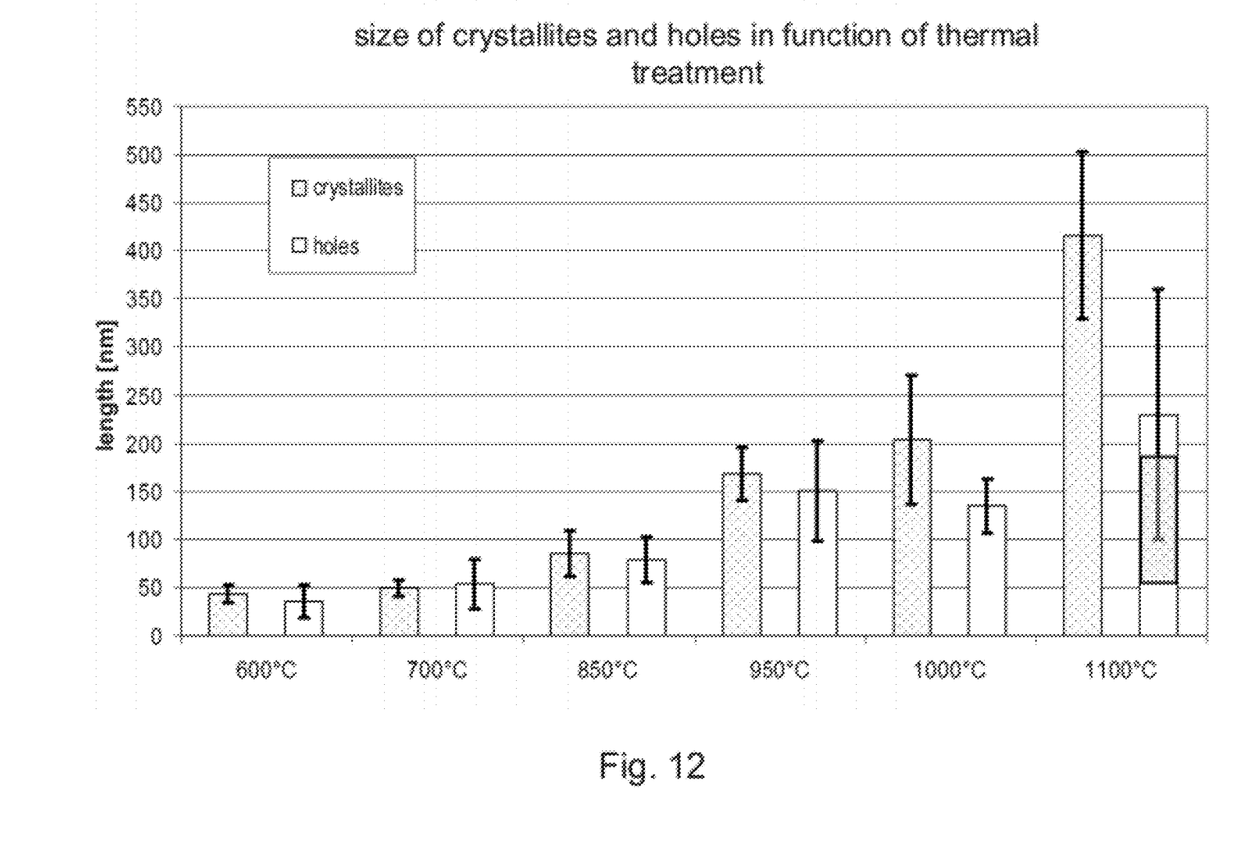
FIG. 12 shows the size of hydroxylapatite crystals as a function of the temperature during annealing.

The invention allows to provide a form-stable hydroxylapatite material, in particular as a granulated material, which comprises crystals having an average diameter from 20 to 600 nm, preferably from 40 to 200 nm (see FIG. 12).

The size of the granules may be adjusted variably, in particular granules can be provided having an average diameter from 0.1 to 10 mm, preferably from 0.5 to 5 mm.

The hydroxylapatite granules with an average diameter between 0.5 and 10 mm is particularly suitable for treating bone defects, especially in the alveolar ridge or in spongy bone defects such as in the femur or tibia.

In a preferred embodiment of the invention, the hydroxylapatite material has a specific surface area from 1 to 100 $m^2/g$, more preferably from 3 to 40 $m^2/g$.

The specific surface area may be measured by $N_2$ adsorption wherein the BET isotherm is used, for example according to DIN ISO 9277.

Figure 4:
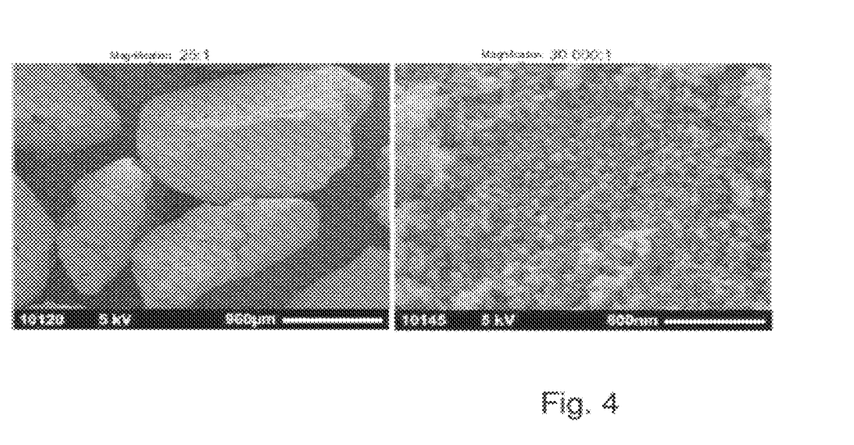
FIG. 4 shows a hydroxylapatite material annealed at 600° C.
Figure 7:
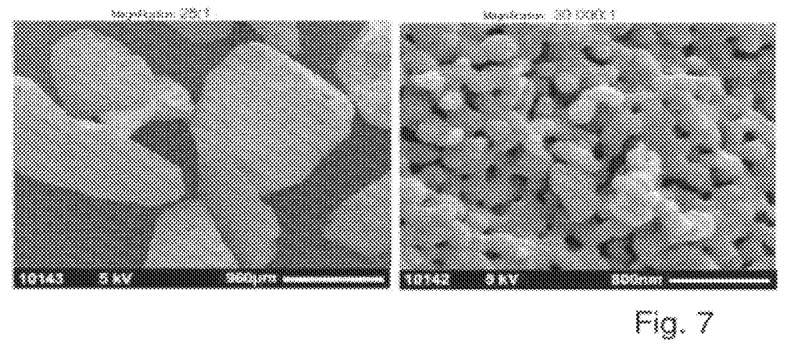
FIG. 7 shows a hydroxylapatite material annealed at 950° C.

Thus, the invention allows to provide a fairly form-stable hydroxylapatite material which has a relatively large surface area and therefore is particularly favorable for formation of natural bone material. The ratio of specific surface area to strength can be adjusted via the temperature of the annealing process. Relatively low temperatures of about 600° C. result in a specific surface area of more than 35 $m^2/g$, whereas a relatively high temperature of 1100° C. yields a specific surface area of less than 1 $m^2/g$. The decrease of the specific surface area is caused by shrinkage of the starting material during the thermal treatment. This results in an increase in pore diameter and a reduction of the number of pores per unit area (FIG. 4, FIG. 7).

The material according to the invention is preferably almost pure hydroxylapatite which comprises at least 90%, preferably at least 95% of hydroxylapatite (wt-%). The atomic ratio of calcium to phosphorus is preferably between 1.6 and 1.7.

Furthermore, the invention relates to an applicator filled with the form-stable hydroxylapatite material.

In particular, this is an applicator having a plunger by means of which the hydroxylapatite material can be pressed out.

DESCRIPTION OF THE DRAWINGS

The invention will now be explained in more detail with reference to the drawings of FIGS. 1 to 12.

Figure 1A:
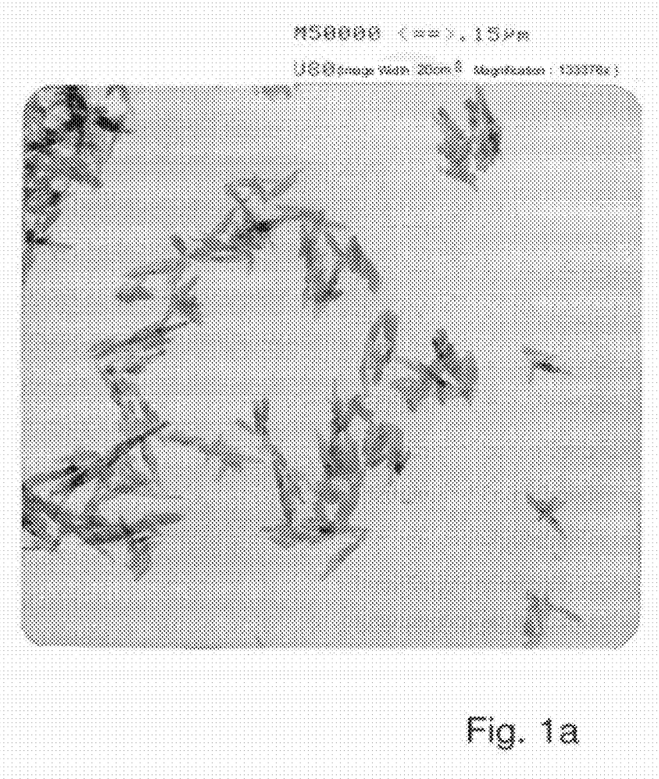

FIG. 1a shows a microscopic view of the starting material (nanoscale hydroxylapatite). The hydroxylapatite is provided as a suspension with needle-shaped particles. The length (longitudinal extension) of the individual particles is on average less than 200 nm, preferably less than 100 nm.

Figure 1B:
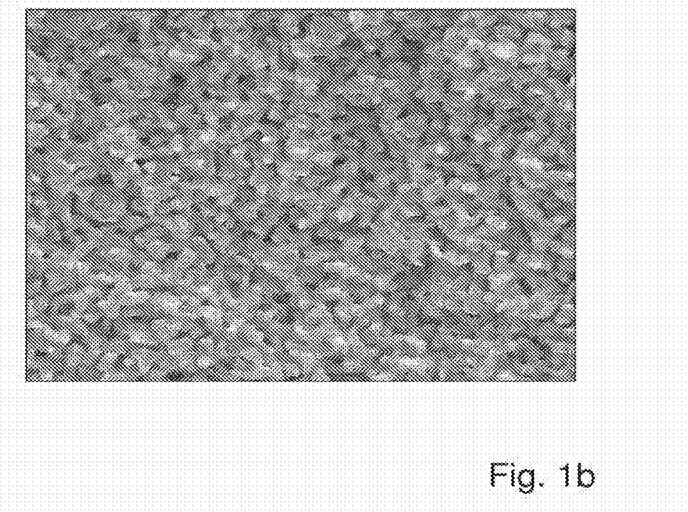

FIG. 1b shows a microscopic view of one embodiment of a hydroxylapatite granulated material according to the invention. Interconnecting dumbbell-shaped or scale-type particles can be seen, so the needle-shaped structure of the starting material is not existent any more.

The material is porous, easily wettable, and well undergoes cohesion.

Due to the relatively small crystals which are similar to those of natural bone mineral, degradation of the material is enhanced.

Figure 2:
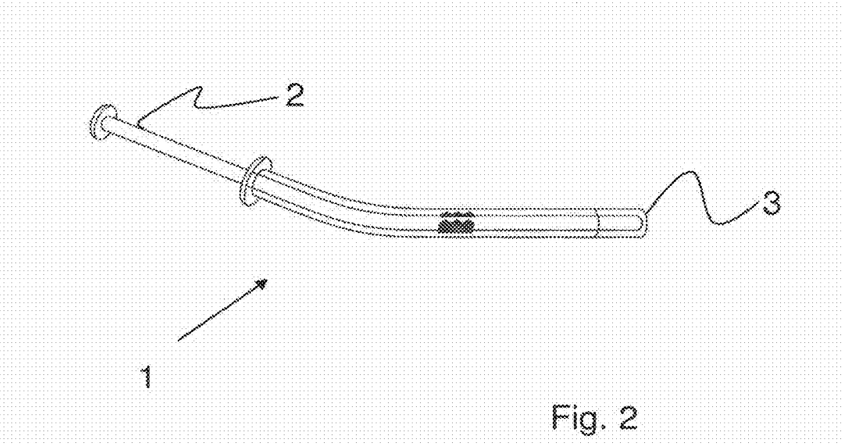
FIG. 2 schematically shows an applicator.

FIG. 2 schematically shows an applicator 1. The applicator comprises a plunger 2 which is introduced into a cylinder from which the hydroxylapatite material is pressed out at outlet 3.

Figure 3:
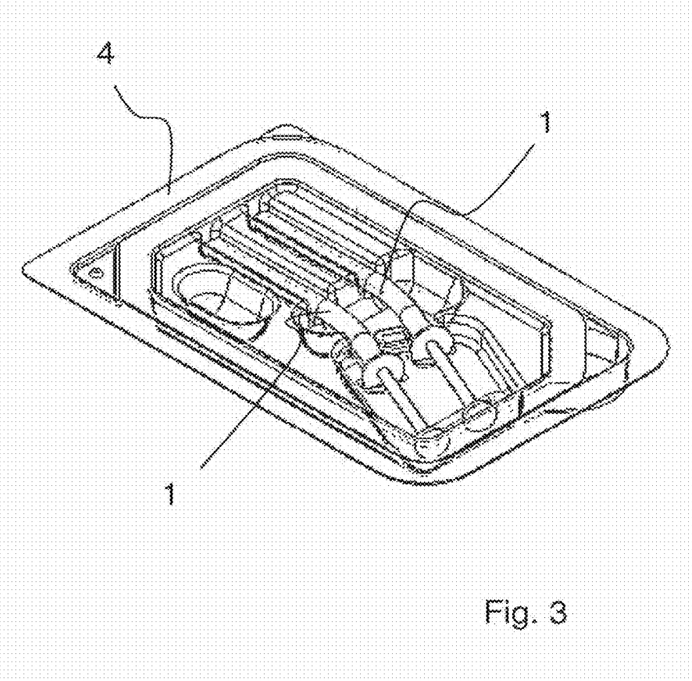
FIG. 3 depicts a tray comprising pre-packaged applicators.

Applicators 1 may be provided pre-packaged in a tray 4, as shown in FIG. 3.

FIGS. 4 through 8 show SEM images for which samples of an inventive hydroxylapatite material of a particle size between 1 and 2 mm were coated with platinum, and were then examined.

Each figure compares two shots, a 25-fold (each image on the left) and a 30,000-fold (image on the right) magnification.

Figure 5:
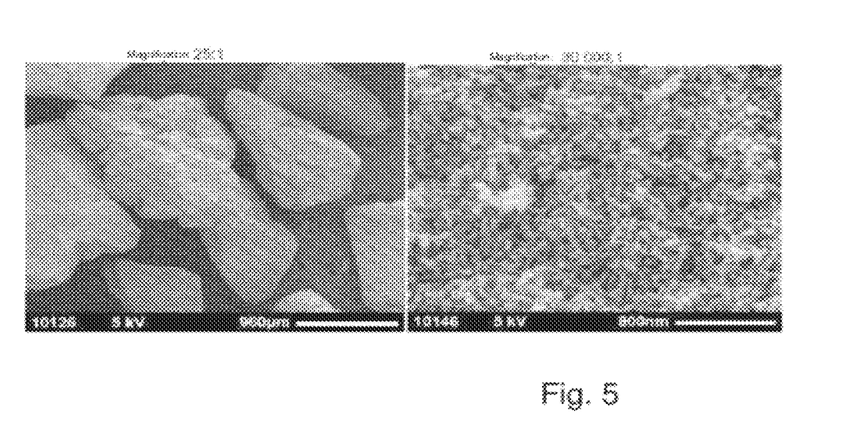
FIG. 5 shows a hydroxylapatite material annealed at 700° C.
Figure 6:
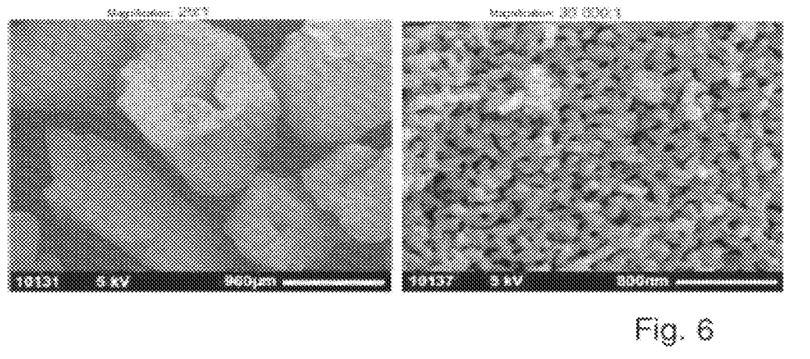
FIG. 6 shows a hydroxylapatite material annealed at 850° C.

FIG. 4 shows a hydroxylapatite material annealed at 600° C.;

FIG. 5 shows a hydroxylapatite material annealed at 700° C.;

FIG. 6 shows a hydroxylapatite material annealed at 850° C.;

FIG. 7 shows a hydroxylapatite material annealed at 950° C.; and

Figure 8:
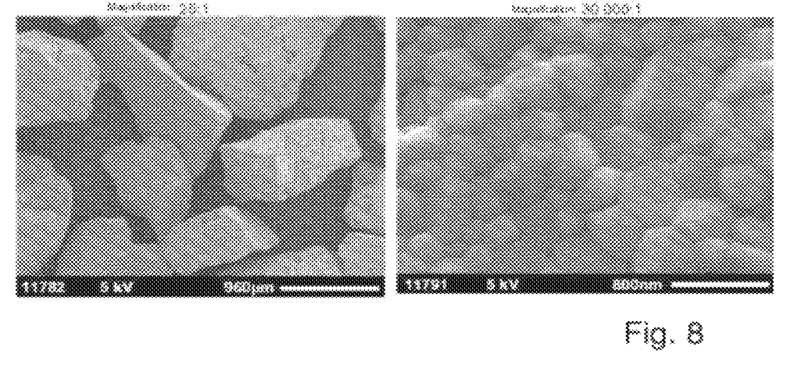
FIG. 8 shows a hydroxylapatite material annealed at 1100° C.

FIG. 8 shows a hydroxylapatite material annealed at 1100° C.

From each of the 25-fold magnifications it can be seen that the shape of the granules is similar, and the particle sizes of the granules decrease with increasing temperature.

From the 30,000-fold magnifications it can be seen that the crystals tend to merge more and more and enlarge in this way. Also, the crystallite size (determined by XRD) increases with temperature, it is from about 20 to 30 nm at 600° C. and reaches 40 to 50 nm at 950° C. The inventors have found that, here, the crystallite size is not only influenced by the temperature but also by the size of the preform bodies prior to the thermal treatment. The material annealed at 950° C. has a smaller surface area and greater strength. At an annealing temperature of 1100° C. the needle-shaped form of the individual crystallites has largely been lost due to sintering.

The strength of granules annealed at 600° C. and 950° C., respectively, was measured in friability tests according to European Pharmacopoeia 6 (chapter 2.9.41, method B). It was found that the granules which had been annealed at 600° C. have a friability F of about 260, a material annealed at 950° C. has a friability F of about 155.

The friability may serve as a measure of processability of the granules, depending on the desired indication.

Preferably, the friability F, also known as friableness, of the hydroxylapatite granulated material is between 80 and 300.

Depending on the indication, by selecting the annealing temperature, inter alia, at least the strength can be adjusted.

Figure 9:
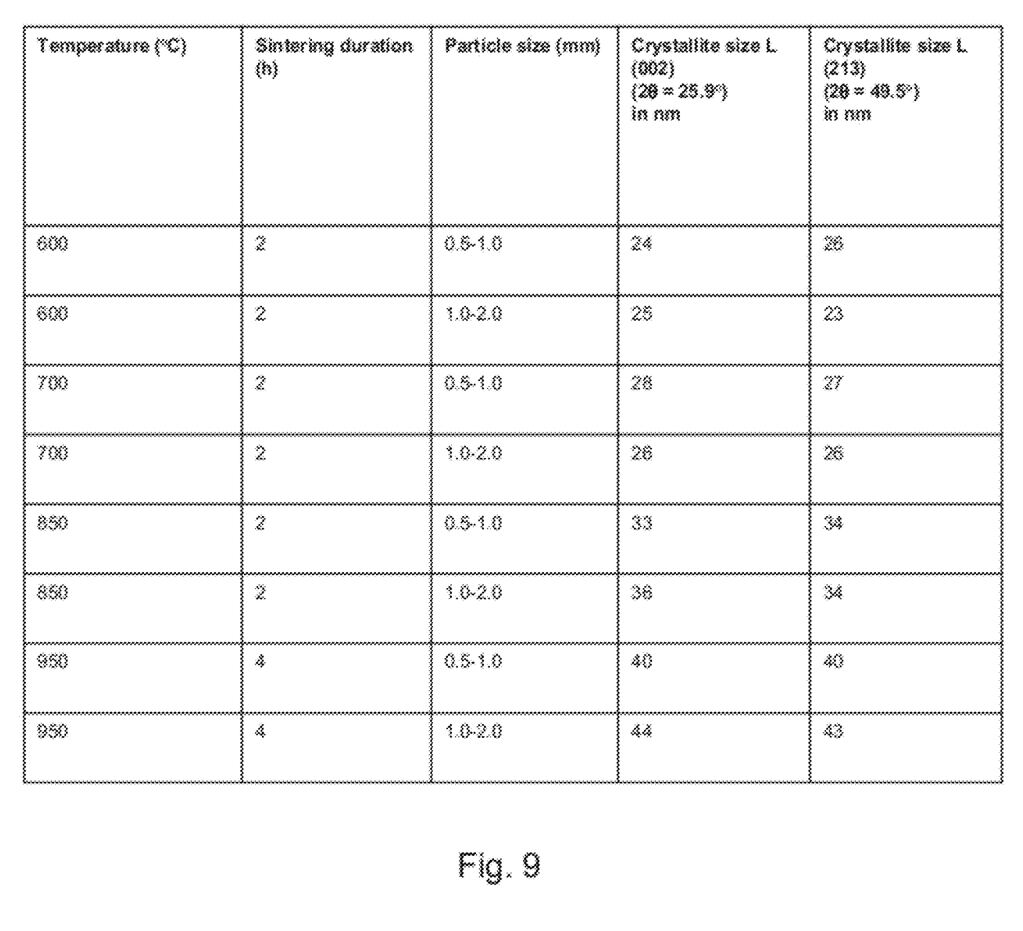
FIG. 9 is a graphic which specifies the crystallite size of different samples.

FIG. 9 shows a table which specifies the crystallite size of different samples. The samples are classified in terms of temperature, annealing time (sintering duration), and particle size. The crystallite size may for example be determined by X-ray diffraction and comparison with the JCPDS database for hydroxylapatite. The crystallite or grain size increases with increasing temperature.

The crystallite size may be calculated using the Scherrer formula, two peaks having been used for the calculation to produce the table represented in FIG. 9: $2\theta=25.9°$ (Miller index (002)), and $2\theta=49.5°$ (Miller index (213)).

Figure 10:
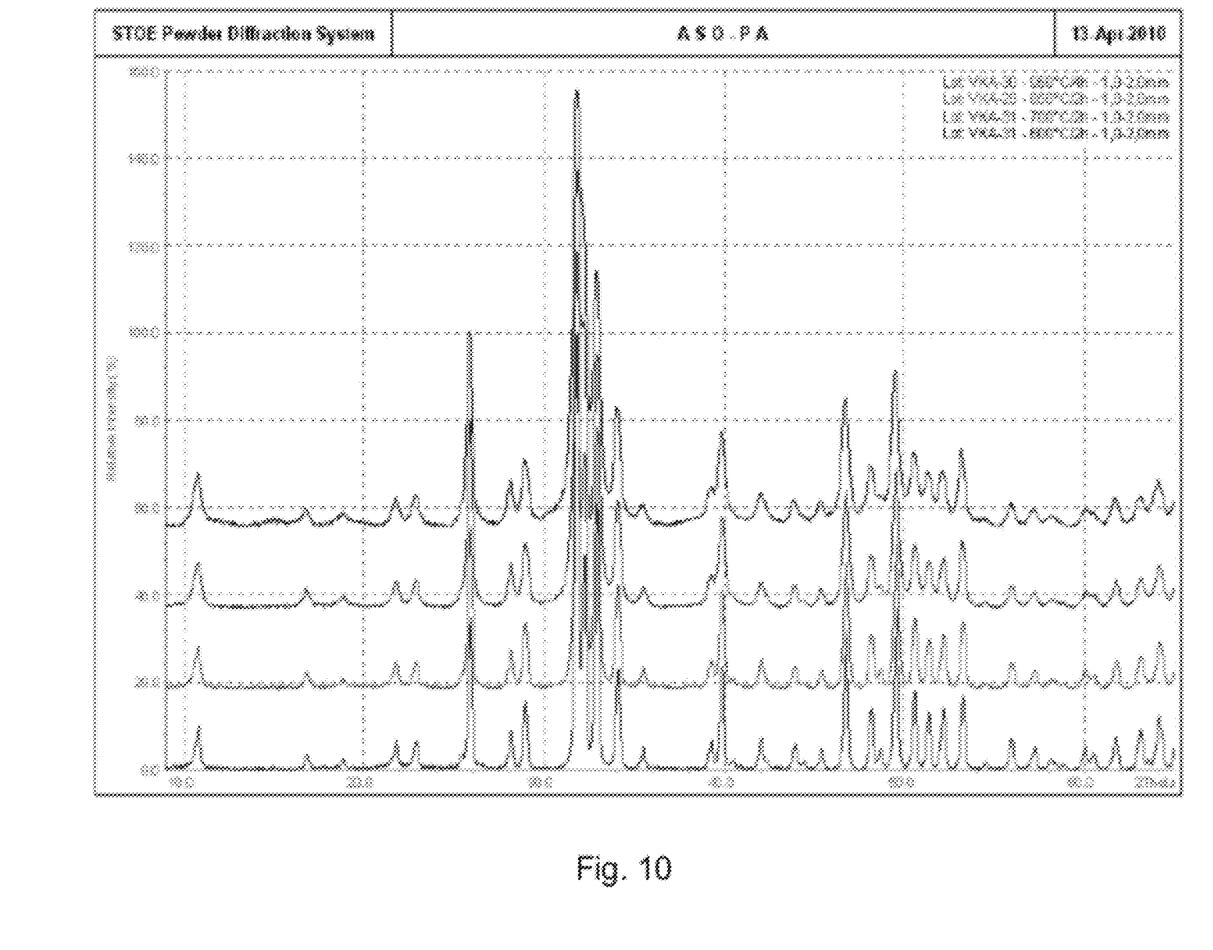
FIG. 10 shows diffraction measurement data.

FIG. 10 shows such diffraction measurement data captured using a diffractometer marketed under the trade name Stadi P by Stoe & CIE company. Reproduced are angles between 9° and 65° (2*theta).

The x-axis represents the angle (2 theta), and the y-axis represents the relative intensity. Compared are 4 curves of a hydroxylapatite material sintered at different temperatures, wherein the material was annealed, from the uppermost to the lowermost curve, at temperatures of: 600° C.; 700° C.; 850° C.; 950° C.

It can be seen that the degree of crystallization increases with increasing annealing temperature, which is represented by a reduction of the peak width.

Figure 11:
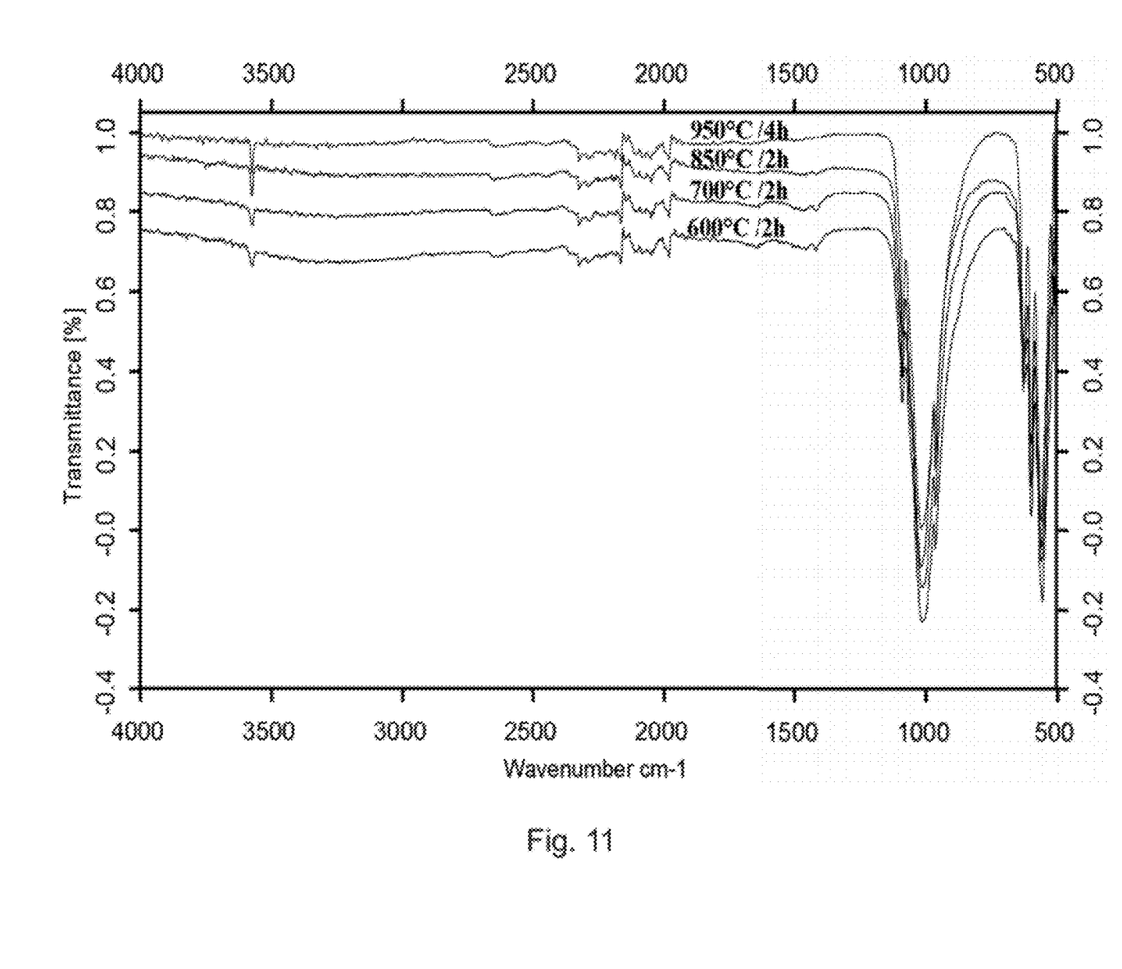
FIG. 11 schematically shows FT infrared spectroscopy plots of different granulated materials.

FIG. 11 schematically shows FT infrared spectroscopy plots of different granulated materials which were also annealed at temperatures between 600° C. (lowermost curve) and 950° C. (uppermost curve). An ATR apparatus by Graseby Specac company and a Bruker IFS28 spectrometer were used.

The infrared spectroscopic images have shown that it is almost pure hydroxylapatite material what is provided. At temperatures between 600° C. and 850° C. there is merely a small peak, if any, due to trapped carbon compounds. Through higher temperatures the carbon compounds are completely removed.

FIG. 12 shows the size of hydroxylapatite crystals in function of the temperature during annealing. On the x-axis granulate materials are plotted which had been annealed at different temperatures, and on the y-axis the length of the crystals (on the left) and holes, or pores (on the right) is compared. It can be seen that by enhanced sintering both the length of the crystals and the diameter of the holes increases. So the average crystal size as well as the hole diameter increases from less than 50 nm at an annealing temperature of 600° C. to about 200 nm at an annealing temperature of 1100° C.

The invention allows to provide a form-stable, easily processable hydroxylapatite granulated material which promotes in-growth of natural bone material and is easy to process.

The invention claimed is:

1. A method for producing a hydroxylapatite material comprising: subjecting a nanoscale hydroxylapatite paste with a solid content ranging from 10% to 60% comprising needle-shaped particles with an average length of less than 200 nm to a thermal treatment at an annealing temperature between 500° C. and 1100 C, which is below a sintering temperature, and with a holding time between 30 minutes and 10 hours, thereby producing a form-stable friable granulated material with a friability F between 50 and 500, wherein said nanoscale hydroxylapatite paste is formed into granule preform bodies prior to the thermal treatment, and wherein a water content of the paste is adjusted so that the paste is sufficiently viscous that the granule preform bodies do not run.

2. The method of claim 1, wherein said thermal treatment is performed at atmospheric pressure.

3. The method of claim 1, wherein said nanoscale hydroxylapatite has a particle size of less than 200 nm as measured along a longitudinal axis thereof.

4. The method of claim 1, wherein said nanoscale hydroxylapatite comprises needle-shaped crystals.

5. The method of claim 1, wherein said form-stable friable granulated material is pressed out into a defect site of a bone by using an application tool comprising a plunger.

6. The method of claim 1, comprising using a granulator to form the granule preform bodies.

* * * * *